(12) United States Patent
Chia et al.

(10) Patent No.: US 8,882,995 B2
(45) Date of Patent: Nov. 11, 2014

(54) PROCESS FOR PREDICTING AND REDUCING THE CORROSIVITY OF A HYDROCARBONACEOUS MIXTURE

(75) Inventors: Lee-Huat Chia, Singapore (SG); Simon Yew-Meng Chooi, Singapore (SG)

(73) Assignee: Shell Oil Company, Houston, TX (US)

( * ) Notice: Subject to any disclaimer, the term of this patent is extended or adjusted under 35 U.S.C. 154(b) by 500 days.

(21) Appl. No.: 13/132,614

(22) PCT Filed: Dec. 3, 2009

(86) PCT No.: PCT/EP2009/066292
§ 371 (c)(1),
(2), (4) Date: Jun. 3, 2011

(87) PCT Pub. No.: WO2010/063786
PCT Pub. Date: Jun. 10, 2010

(65) Prior Publication Data
US 2011/0259798 A1    Oct. 27, 2011

(30) Foreign Application Priority Data
Dec. 5, 2008  (EP) ..................... 08170784

(51) Int. Cl.
C10G 19/02 (2006.01)
C10G 75/00 (2006.01)
C10G 75/02 (2006.01)
G01N 33/28 (2006.01)
G01N 30/14 (2006.01)

(52) U.S. Cl.
CPC ............ *G01N 33/2835* (2013.01); *C10G 75/00* (2013.01); *C10G 75/02* (2013.01); *C10G 19/02* (2013.01); *C10G 2300/202* (2013.01); *C10G 2300/4075* (2013.01); *G01N 2030/143* (2013.01)
USPC .............................. 208/263; 208/47; 208/292

(58) Field of Classification Search
USPC ................... 208/47, 187, 263, 292
See application file for complete search history.

(56) References Cited

U.S. PATENT DOCUMENTS

| | | | |
|---|---|---|---|
| 6,281,328 B1 | 8/2001 | Sartori et al. | ................. 528/492 |
| 2007/0298505 A1* | 12/2007 | Smith et al. | ..................... 436/61 |
| 2008/0257782 A1* | 10/2008 | Vachhani et al. | .............. 208/47 |

FOREIGN PATENT DOCUMENTS

| | | | |
|---|---|---|---|
| EP | 1840567 | 10/2007 | ............. G01N 33/28 |
| EP | 1870706 | 12/2007 | ............. G01N 30/06 |
| RU | 2130915 | 5/1999 | |
| RU | 2275417 | 4/2006 | |
| WO | WO0218519 | 3/2002 | ............. C10G 53/12 |

OTHER PUBLICATIONS

Borgund, Anna E. et al. "Fractionation of Crude Oil Acids by HPLC and Characterization of Their Properties and Effects on Gas Hydrate Surfaces" Energy & Fuels Jul. 2007, 21, 2816-2826.*
Babaian-Kibala, Elizabeth. "Phosphate Ester Inhibitors Solve Naphthenic Acid Corrosion Problems", Oil & Gas Journal, 92:9, Feb. 1994.*
Rohm and Haas, Amberlyst(TM) Polymeric Catalysts and Ion Exchange Resins, no date, retrieved from http://www.amberlyst.com/sac.htm Apr. 9, 2014.*
Jones, D.M. et al.; "Determination of Naphthenic Acids in Crude Oils Using Nonaqueous Ion Exchange Solid-Phase Extraction"; Analytical Chemistry, American Chemical Society; Columbus; vol. 73, No. 3 ; pp. 703-707, XP002453019 ISSN: 0003-2700; Jan. 1, 2001.
Borgund et al; "Normal Phase High Performance Liquid Chromatography for Fractionation of Organic Acid Mixtures Extracted from Crude Oils"; Journal of Chromatography; Elsevier Science Publishers B.V.; Amsterdam, NL; vol. 1149, No. 2; pp. 189-196; XP022047975 ISSN: 0021-9673; Apr. 26, 2007.
Saab, J. et al.; "Quantitative Extraction Procedure of Naphthenic Acids Contained in Crude Oils. Characterization with Different Spectroscopic Methods"; Energy & Fuels, the Society, Washington, DC; vol. 19, No. 2; pp. 525-531; XP002453022 ISSN: 0887-0624 "2. Experimental Section" Jan. 1, 2005.

* cited by examiner

*Primary Examiner* — Renee E Robinson
(74) *Attorney, Agent, or Firm* — Charles W. Stewart

(57) ABSTRACT

Process for reducing the concentration of water-soluble carboxylic acids in a hydrocarbonaceous mixture which process comprises (i) taking a sample from the hydrocarbonaceous mixture and extracting the water-soluble carboxylic acids from the sample, (ii) subjecting the extracted water-soluble carboxylic acids to chromatography, (iii) calculating the concentration of water-soluble carboxylic acids in the hydrocarbon mixture based on the chromatography results, and (iv) reducing the concentration of water-soluble carboxylic acids in the hydrocarbonaceous mixture.

14 Claims, No Drawings

PROCESS FOR PREDICTING AND REDUCING THE CORROSIVITY OF A HYDROCARBONACEOUS MIXTURE

PRIORITY CLAIM

The present application claims priority from PCT/EP2009/066292, filed 3 Dec. 2009, which claims priority from European Application 08170784.6, filed 5 Dec. 2008.

TECHNICAL FIELD OF THE INVENTION

The present invention relates to a process for reducing the concentration of water-soluble carboxylic acids of a hydrocarbonaceous mixture.

The so-called Total Acid Number (TAN) of a hydrocarbonaceous mixture measured according to ASTM D974 and/or ASTM D664, tends to be considered the appropriate indication for its corrosivity. However, it is cumbersome and time-consuming to determine the TAN number. Therefore, it is often not possible to determine the TAN number before a hydrocarbonaceous mixture enters a refinery. This makes that some highly corrosive mixtures are not spotted resulting in damage to conduits and storage tanks. The problem is especially pronounced in conduits and storage tanks for crude oils and condensates, especially in conduits for transport from offshore to onshore storage tanks and to the onshore storage tanks receiving such crude oil or condensate. Furthermore, the TAN test method does not only identify carboxylic acids but also compounds which per se are less problematic from a corrosion point of view such as phenols and mercaptans.

Further prior art methods for determining corrosivity such as the one described in U.S. Pat. No. 7,160,72 are cumbersome and time-consuming as well.

EP-A-1840567 and EP-A-1870706 teach to measure the amount of naphthenic acids in order to characterise a crude oil. Naphthenic acids are not water soluble and are difficult to extract.

We have now surprisingly found that the corrosivity of a hydrocarbonaceous mixture, more especially crude oils and condensates, can be determined by only measuring the concentration of water-soluble carboxylic acids of the hydrocarbonaceous mixture in a simple and efficient way. Based on the concentration found, it can be decided whether the concentration of water-soluble carboxylic acids in the hydrocarbonaceous mixture is to be reduced.

Therefore, the present invention relates to a process for reducing the concentration of water-soluble carboxylic acids in a hydrocarbonaceous mixture which process comprises
(i) taking a sample from the hydrocarbonaceous mixture and extracting the water-soluble carboxylic acids from the sample,
(ii) subjecting the extracted water-soluble carboxylic acids to chromatography,
(iii) calculating the concentration of water-soluble carboxylic acids in the hydrocarbon mixture based on the chromatography results, and
(iv) reducing the concentration of water-soluble carboxylic acids in the hydrocarbonaceous mixture based on the calculated concentration of water-soluble carboxylic acids in the hydrocarbon mixture.

The essence of the present invention is that although it is well known that acids are corrosive and it is known how to determine the concentration of water-soluble carboxylic acids, we have found that it suffices to establish the concentration of water-soluble carboxylic acids in order to determine whether the acidity of the oil fraction is a problem under specific circumstances. If so, the concentration of water-soluble carboxylic acids can be reduced.

Water-soluble carboxylic acids are non-aromatic acids generally comprising of from 1 to 7 carbon atoms.

It was found that this process was especially useful for predicting the corrosivity of crude oils and condensates further comprising water. The amount of water can vary widely but will generally be at least 0.1% by weight on total amount of hydrocarbonaceous mixture, more specifically at least 0.2% by weight, more specifically at least 0.3% by weight, most specifically at least 0.4% by weight. Generally, the amount of water will be at most 2% by weight, more specifically at most 1.5% by weight, more specifically at most 1% by weight, most specifically less than 1% by weight.

There are various suitable methods for extracting the water-soluble carboxylic acids from the sample. Preferably, the methods extract the water-soluble carboxylic acids while the water-insoluble carboxylic acids such as the naphthenic acids, remain in the sample. One of these methods comprises subjecting the sample to solid phase extraction thereby extracting the water-soluble carboxylic acids and subsequently eluting the extracted carboxylic acids from the solid phase with the help of a solvent and determining their weight amount. The solid phase extraction can be carried out with the help of solid phase extraction cartridges commercially available and known to be suitable to someone skilled in the art such as the Sep-Pak aminopropyl cartridges available from Waters Corporation, USA. The solid phase can be conditioned before use such as by treating with an appropriate solvent such as dichloromethane. Preferably, the hydrocarbonaceous sample is dissolved in this solvent and contacted with the cartridge. During elution, further solvent can be added.

The extracted carboxylic acids are subsequently to be removed from the solid phase with the help of a solvent suitable for doing so. Someone skilled in the art will know which solvents or mixture or sequence of solvents are suitable. A solvent which can be used is acetone followed by a mixture of acetone and methanol followed by methanol.

A preferred method for extracting the water-soluble carboxylic acids is with the help of an aqueous solution, preferably with the help of an aqueous solution having a pH of more than 7. It was found that the sample only needs to be treated twice with a volume of aqueous solution similar to the volume of the sample if the aqueous solution had a pH of at least 8 and only once if the aqueous solution had a pH of at least 9. Preferably, the aqueous solution is a metal hydroxide solution such as a sodium hydroxide solution. Additionally, demulsifier can be present in the aqueous solution or can be added to the hydrocarbonaceous sample in order to improve the separation of the hydrocarbonaceous phase from the aqueous phase. Demulsifiers are commercially available.

The water soluble carboxylic acids can then be quantified by chromatography. Someone skilled in the art will know which chromatography methods are suitable for use in the present invention. A method which can be used is so-called ion exclusion chromatography.

Ion exclusion chromatography is well known in the art. For the present invention, it involves the use of a column which has been calibrated for each of the carboyxlic acids before the extracted acids are subjected to it so that the it shows the amount of each of the water-soluble carboxylic acids present in the sample. A suitable column is a polystyrene-divinylbenzene co-polymer having sulfonic groups. An elution solvent which can be applied is a mixture of dilute sulphuric acid and acetone. Someone skilled in the art will know which other columns and elution solvents can be used. The total concentration of water-soluble carboxylic acids in the hydrocarbonaceous mixture can be found by adding together the concentrations of the individual water-soluble carboxylic acids.

On basis of the extraction efficiency applied and the amount of water-soluble carboxylic acids which were extracted, someone skilled in the art can establish the amount of water-soluble carboxylic acids in the hydrocarbonaceous sample. From this can be deduced the concentration of water-soluble carboxylic acids present in the hydrocarbonaceous mixture. A formula for calculating the amount of water-soluble carboxylic acids in the hydrocarbonaceous mixture is as follows:

$$Conc(\text{acids}) = \frac{\text{mass (acids)}}{\text{mass (sample)} \times \textit{Eff}.}$$

wherein Conc(acids) is the concentration water-soluble carboxylic acids, Eff. is the ratio of water-soluble carboxylic acids extracted to water-soluble carboxylic acids present, mass (sample) is the weight amount of the hydrocarbonaceous sample and mass (acids) is the weight amount of extracted water-soluble carboxylic acids determined with the help of a chromatograph. Eff. is established empirically for the chosen extraction method.

If water-soluble carboxylic acids are found to be present, the hydrocarbonaceous mixture is potentially corrosive and may need to be treated before entering the refinery. In many instances solely steps (i)-(iii) are carried out. Step (iv) will only be applied if the concentraction of water-soluble carboxylic acids is judged to be too high depending i.a. on the subsequent use of the hydrocarbonaceous mixture. The mixture will be treated if the concentration of water-soluble carboxylic acid is considered relatively high and if the mixture will remain in the tank for some time. In most cases, step (iv) will be applied if the amount of water-soluble carboxylic acids found to be present is at least 1 part per million by weight (ppmw).

Many processes are known for reducing the concentration of water-soluble carboxylic acids in the hydrocarbonaceous mixture. A process which is especially effective is a process which comprises (a) determining the corrosivity of the hydrocarbonaceous mixture with the help of a process according to the present invention as described above, (b) adding to the hydrocarbonaceous mixture an amount of base sufficient to neutralise the water-soluble carboxylic acids in the hydrocarbonaceous mixture, and optionally (c) removing carboxylate salts from the hydrocarbonaceous mixture. An especially efficient method is a process in which the hydrocarbonaceous mixture subjected to step (c) comprises water, and step (c) comprises removing carboxylate salts by separating aqueous solution from the hydrocarbonaceous mixture. In such process, the base added in step (b) preferably is an aqueous solution having a pH of more than 7, preferably at least 8, more preferably at least 9. Preferably, the aqueous solution is a metal hydroxide solution such as a sodium hydroxide solution. Additionally, a demulsifier can be present in the aqueous solution or can be added to the hydrocarbonaceous mixture in order to improve the separation of the hydrocarbonaceous phase from the aqueous phase.

An alternative method for reducing the corrosivity of the hydrocarbonaceous mixture containing water-soluble carboxylic acids comprises (a) determining the concentration of water-soluble carboxylic acids in the hydrocarbonaceous mixture with the help of a process according to the present invention as described above, and (b) adding corrosion inhibitor to the hydrocarbonaceous mixture to neutralise the water-soluble carboxylic acids. The corrosion inhibitor is preferably added just before the hydrocarbonaceous mixture enters the conduit or vessel. Corrosion inhibitors are commercially available. Preferred corrosion inhibitors are phosphate esters.

An especially efficient method for reducing the concentration of water-soluble carboxylic acids in a hydrocarbonaceous mixture can be applied if water is present. The water may be present in the hydrocarbonaceous mixture or may be added. This method comprises (a) determining the concentration of water-soluble carboxylic acids in the hydrocarbonaceous mixture with the help of the present invention and (b) separating water from the hydrocarbonaceous mixture. Again, demulsifier can be present in the aqueous solution or can be added to the hydrocarbonaceous mixture in order to improve the separation of the hydrocarbonaceous phase from the aqueous phase.

A further method for reducing the concentration of water-soluble carboxylic acids in a hydrocarbonaceous mixture containing water-soluble carboxylic acids comprises determining the concentration of water-soluble carboxylic acids in the hydrocarbonaceous mixture with the help of the present invention, and (b) blending the hydrocarbonaceous mixture with a further hydrocarbonaceous mixture containing a minor amount of water-soluble carboxylic acids. Further hydrocarbonaceous mixtures which can be used are mixtures containing less than 1 part per million by weight (ppm) of water-soluble carboxylic acids.

The invention will hereinafter be described by means of the following non-limiting example.

EXAMPLE

An undersea pipeline was used for transporting crude oil from tanker ships to the storage tanks of a refinery without measures being taken to prevent corrosion of the pipeline.

Inspection showed that the corrosion at the bottom of the pipe-line was such that the thickness at the bottom reduced at an average corrosion rate of 0.21 mm/year. The corrosion was measured at the bottom of the pipe-line as water is heavier than crude oil.

Subsequently, the corrosivity of the crude oil was checked in accordance with the present invention and reduced if appropriate. It was found that the average corrosion rate was strongly reduced.

What is claimed is:
1. Process for predicting and reducing the corrosivity of a hydrocarbonaceous mixture comprising crude oil and/or condensates and water, which process comprises:
   (i) taking a sample from the hydrocarbonaceous mixture comprising crude oil and/or condensates and 0.1% to 2.0% by weight water and extracting water-soluble carboxylic acids comprising non-aromatic acids having from 1 to 7 carbon atoms from the sample with the help of an aqueous solution,
   (ii) subjecting the extracted water-soluble non-aromatic carboxylic acids to chromatography,
   (iii) calculating the concentration of water-soluble non-aromatic carboxylic acids in the hydrocarbonaceous mixture based on the chromatography results, and
   (iv) reducing the concentration of water-soluble non-aromatic carboxylic acids in the hydrocarbonaceous mixture based on the calculated concentration of water-soluble non-aromatic carboxylic acids in the hydrocarbonaceous, thereby reducing the corrosivity of the hydrocarbonaceous mixture.

2. Process according to claim 1, in which process the concentration of water soluble non-aromatic carboxylic acids is reduced to less than 1 ppmw.

3. Process according to claim 2, in which the concentration of water-soluble non-aromatic carboxylic acids is determined by ion exchange chromatography using a column containing a polystyrene-divinylbenzene co-polymer having sulfonic groups.

4. Process according to claim 3, in which process the hydrocarbonaceous mixture comprises at least about 0.4% to 2.0% by weight water.

5. Process according to claim 4, in which process step (i) is carried out by subjecting the sample to solid phase extraction to extract the water-soluble non-aromatic carboxylic acids and subsequently eluting the extracted non-aromatic carboxylic acids from the solid phase with the help of a solvent and subjecting the eluted water-soluble non-aromatic carboxylic acids to step (ii).

6. Process according to claim 4, in which process step (i) is carried out by extracting the water-soluble non-aromatic carboxylic acids from the sample with the help of an aqueous solution having a pH more than 7, which extracted water-soluble non-aromatic carboxylic acids are subjected to step (ii).

7. Process according to claim 6, in which the aqueous solution has a pH of at least 8.

8. Process according to claim 7, in which process step (iv) comprises adding to the hydrocarbonaceous mixture an amount of base sufficient to neutralise the water-soluble non-aromatic carboxylic acids in the hydrocarbonaceous mixture.

9. Process according to claim 8, in which process the hydrocarbonaceous mixture subjected to step (iv) comprises water, and step (iv) comprises removing carboxylate salts by separating aqueous solution from the hydrocarbonaceous mixture.

10. Process according to claim 7, in which process step (iv) comprises adding corrosion inhibitor to the hydrocarbonaceous mixture to neutralise the water-soluble non-aromatic carboxylic acids.

11. Process according to claim 10, in which process the corrosion inhibitor is a phosphate ester.

12. Process according to claim 7, in which process step (iv) comprises separating water from the hydrocarbonaceous mixture.

13. Process according to claim 7, in which process step (iv) comprises blending the hydrocarbonaceous mixture with hydrocarbons containing less water-soluble non-aromatic carboxylic acids.

14. Process according to claim 3, in which the column is calibrated for each of the water-soluble carboxylic acids before the extracted acids are subjected to it so that it will show the amount of each water-soluble carboxylic acid present in the sample.

* * * * *